United States Patent
Kobayashi et al.

(10) Patent No.: US 9,821,434 B2
(45) Date of Patent: Nov. 21, 2017

(54) SHOT PEENING METHOD, SHOT PEENING EVALUATION METHOD, AND SHOT PEENING EVALUATION ASSEMBLY STRUCTURE

(71) Applicant: Sintokogio, Ltd., Nagoya-shi, Aichi (JP)

(72) Inventors: Yuji Kobayashi, Toyokawa (JP); Akinori Matsui, Toyokawa (JP)

(73) Assignee: SINTOKOGIO, LTD., Nagoya-shi, Aichi (JP)

( * ) Notice: Subject to any disclaimer, the term of this patent is extended or adjusted under 35 U.S.C. 154(b) by 0 days.

(21) Appl. No.: 15/270,642

(22) Filed: Sep. 20, 2016

(65) Prior Publication Data
US 2017/0008149 A1    Jan. 12, 2017

Related U.S. Application Data (62) Division of application No. 14/395,918, filed as application No. PCT/JP2013/067162 on Jun. 18, 2013, now Pat. No. 9,486,894.

(30) Foreign Application Priority Data

Jun. 27, 2012  (JP) ................................. 2012-144572

(51) Int. Cl.
*B24C 1/10*        (2006.01)
*B24C 3/32*        (2006.01)
(Continued)

(52) U.S. Cl.
CPC ................ *B24C 1/10* (2013.01); *B22D 17/22* (2013.01); *B24C 3/325* (2013.01); *C21D 7/06* (2013.01);
(Continued)

(58) Field of Classification Search
CPC .. B24C 1/04; B24C 1/10; B24C 3/325; B24C 3/327; C21D 7/06; B22D 17/22;
(Continued)

(56) References Cited

U.S. PATENT DOCUMENTS

| | | |
|---|---|---|
| 5,172,580 A | 12/1992 | Thompson |
| 6,502,449 B1 | 1/2003 | Baiker |

(Continued)

FOREIGN PATENT DOCUMENTS

| | | |
|---|---|---|
| CN | 1317091 | 5/2007 |
| CN | 101778700 | 7/2010 |

(Continued)

*Primary Examiner* — Peter DungBa Vo
*Assistant Examiner* — Joshua D Anderson
(74) *Attorney, Agent, or Firm* — Drinker Biddle & Reath LLP (57) ABSTRACT

In a trial peening step, a shot peening process is applied to a back face 40B of a mold 40 in which an opening of a closed-end water cooling hole 42 is formed. Next, in an evaluation step, compressive residual stress and surface roughness of a region shot-peened in the trial peening step are measured and an extent of shot peening treatment in the trial peening step is evaluated based on measurement results. Next, in a peening step, a surface of the water cooling hole 42 in the mold 40 is shot-peened under peening conditions set based on peening conditions for the trial peening step and on evaluation results produced in the evaluation step.

2 Claims, 4 Drawing Sheets

(51) Int. Cl.
*C21D 7/06* (2006.01)
*B22D 17/22* (2006.01)

(52) U.S. Cl.
CPC ....... *G01N 2203/008* (2013.01); *Y10T 29/479* (2015.01)

(58) Field of Classification Search
CPC .............. B22D 17/2218; B24B 39/006; G01N 2203/008; B21D 31/06; Y10T 29/479
USPC .... 72/14.8, 4.9, 15.3, 16.1, 16.2, 16.4, 17.3, 72/18.1, 18.6, 18.7, 19.6, 19.7, 53; 29/90.7
See application file for complete search history.

(56) References Cited

U.S. PATENT DOCUMENTS

| | | | |
|---|---|---|---|
| 6,502,499 B2 | 1/2003 | Sannomiya et al. | |
| 6,568,239 B1 | 5/2003 | Champaigne | |
| 2010/0077831 A1 | 4/2010 | Bailey et al. | |

FOREIGN PATENT DOCUMENTS

| | | |
|---|---|---|
| CN | 102341217 | 2/2012 |
| DE | 3615560 A1 | 11/1987 |
| JP | S61-50771 A | 3/1986 |
| JP | S61-249274 A | 11/1986 |
| JP | H07-128037 A | 5/1995 |
| JP | 7-290222 A | 11/1995 |
| JP | 2003-159651 A | 6/2003 |
| JP | 2004-045115 A | 2/2004 |
| JP | 2004-142007 A | 5/2004 |
| JP | 2009-236822 A | 10/2009 |
| JP | 2010-142899 A | 7/2010 |
| JP | 2011-033582 A | 2/2011 |
| JP | 2015-104775 | 6/2015 |
| TW | 201127557 | 8/2011 |
| TW | 201208817 | 3/2012 |
| WO | WO 2012-056913 | 5/2012 |
| WO | WO-2013/175660 A1 | 11/2013 |

SHOT PEENING METHOD, SHOT PEENING EVALUATION METHOD, AND SHOT PEENING EVALUATION ASSEMBLY STRUCTURE

TECHNICAL FIELD

The present invention relates to a shot peening method, shot peening evaluation method, and shot peening evaluation assembly structure.

BACKGROUND ART

Conventionally, a shot peening process has been used in various fields, where the shot peening process involves impacting a surface of a workpiece with hard balls of metal, ceramic or the like at high velocities to harden the surface of the metal workpiece. By impacting the workpiece surface with hard balls at high velocities, the shot peening process forms a compressively stressed portion on the workpiece surface with a residual compressive stress imparted thereto, and thereby hardens the workpiece surface and improves its wear resistance.

Patent Literature 1 describes a casting mold whose cooling water passage is subjected to a shot peening process on a surface layer and thereby imparted with a residual compressive stress. In the casting mold, the shot peening process is applied to the surface layer of the cooling water passage to increase fatigue strength against tensile stress produced on the surface layer of the cooling water passage and thereby prevent cracks.

CITATION LIST

Patent Literature

Patent Literature 1: Japanese Patent Application Laid-Open Publication No. 07-290222

SUMMARY OF INVENTION

Technical Problem

In order to impart sufficient residual compressive stress to the surface of the cooling water passage, it is necessary to perform the shot peening process under appropriate peening conditions. For example, molds sometimes undergo a nitriding process to improve their wear resistance, but if the molds subjected to such a nitriding process are shot-peened excessively, a nitrided layer on a mold surface might be removed, making it impossible to impart residual compressive stress effectively to the surface of the cooling water passage. However, the shot peening treatment method described in Patent Literature 1 does not give consideration to peening conditions for applying appropriate treatment to the surface of the water cooling hole and has room for improvement from the viewpoint of shot-peening the surface of the water cooling hole under desirable peening conditions.

An object of the present invention is to provide a shot peening method which can shot-peen a surface of a water cooling hole under desirable peening conditions or to provide a shot peening evaluation method or shot peening evaluation assembly structure which can be used to set desirable peening conditions for the surface of the water cooling hole.

Solution to Problem

A shot peening method according to one aspect of the present invention comprises: a trial peening step of shot-peening a back face of a mold in which an opening of a closed-end water cooling hole is formed; an evaluation step of measuring at least one of compressive residual stress and surface roughness of a region shot-peened in the trial peening step and evaluating an extent of shot peening treatment in the trial peening step based on measurement results, the evaluation step being carried out after the trial peening step; and a peening step of shot-peening a surface of the water cooling hole under peening conditions set based on peening conditions for the trial peening step and on evaluation results produced in the evaluation step, the peening step being carried out after the evaluation step.

With the shot peening method according to one aspect of the present invention, the trial peening step involves shot-peening the back face of the mold in which the opening of the closed-end water cooling hole is formed. In the evaluation step after the trial peening step, at least one of compressive residual stress and surface roughness of the region shot-peened in the trial peening step is measured and the extent of shot peening treatment in the trial peening step is evaluated based on the measurement results. In the peening step after the evaluation step, the surface of the water cooling hole in the mold is shot-peened under the peening conditions set based on the peening conditions for the trial peening step and the evaluation results produced in the evaluation step. This makes it possible to shot-peen the surface of the water cooling hole under desirable peening conditions.

In the shot peening method according to one aspect of the present invention, the trial peening step and the evaluation step may be carried out alternately a plurality of times before the peening step; and in the peening step, the surface of the water cooling hole may be shot-peened under the peening conditions set based on the peening conditions for the trial peening step repeated a plurality of times and on the evaluation results produced in the evaluation step repeated a plurality of times.

With the shot peening method according to one aspect of the present invention, the trial peening step and the evaluation step are carried out alternately a plurality of times before the peening step. Then, in the peening step, the surface of the water cooling hole in the mold is shot-peened under the peening conditions set based on the peening conditions for the trial peening step repeated a plurality of times and on the evaluation results produced in the evaluation step repeated a plurality of times. In this way, since the peening conditions for the peening step are set based on the peening conditions for the trial peening step repeated a plurality of times and on the evaluation results produced in the evaluation step repeated a plurality of times, the surface of the water cooling hole can be shot-peened under more desirable peening conditions.

The shot peening method according to one aspect of the present invention may further comprise: a jig fixing step of fixing a jig in which a through-hole is formed to the back face of the mold with an open end of the through-hole turned to the back face of the mold, where the through-hole is set to be equal in diameter and depth to the water cooling hole; a trial nozzle-insertion step of inserting a shot peening nozzle into the through-hole after the jig fixing step; and a nozzle insertion step of inserting the shot peening nozzle into the water cooling hole after the evaluation step, wherein the jig fixing step and the trial nozzle-insertion step are preparatory steps before starting the trial peening step, and the nozzle insertion step is a preparatory step before starting the peening step.

With the shot peening method according to one aspect of the present invention, the jig fixing step and trial nozzle-insertion step are carried out as preparatory steps before starting the trial peening step. In the jig fixing step, a jig in which a through-hole set to be equal in diameter and depth to the water cooling hole is formed is fixed to the back face of the mold with the open end of the through-hole turned to the back face of the mold. In the trial nozzle-insertion step carried out after the jig fixing step, a shot peening nozzle is inserted into the through-hole. Also, the nozzle insertion step is carried out as a preparatory step before starting the peening step. In the nozzle insertion step carried out after the evaluation step, the shot peening nozzle is inserted into the water cooling hole. This allows the high-velocity shot media to hit a bottom of the water cooling hole even if the water cooling hole is small in diameter and deep. Also, a practical trial of the nozzle insertion step is carried out in the trial nozzle-insertion step, a practical trial of the peening step is carried out in the trial peening step, and the extent of shot peening treatment in the trial peening step is evaluated in the evaluation step, making it possible to avoid excessive application of the shot peening process.

In the shot peening method according to one aspect of the present invention, in the jig fixing step, pressing forces directed toward where the jig and the back face of the mold face each other may be imparted to a sealing unit placed by surrounding the open end of the through-hole in an opposing area between the jig and the back face of the mold.

With the shot peening method according to one aspect of the present invention, since in the jig fixing step, pressing forces directed toward where the jig and the back face of the mold face each other are imparted to the sealing unit placed by surrounding the open end of the through-hole in the opposing area between the jig and the back face of the mold, the sealing unit prevents air leakage from between the jig and the back face of the mold during the shot peening process in the trial peening step. That is, the trial peening step can be carried out in an environment configured to more closely approximate that of the peening step. This makes it possible to improve accuracy of the peening conditions to be set.

A shot peening evaluation method according to one aspect of the present invention comprises: a trial peening step of shot-peening a back face of a mold in which an opening of a closed-end water cooling hole is formed, the trial peening step being carried out before shot-peening a surface of the water cooling hole in the mold; and an evaluation step of measuring at least one of compressive residual stress and surface roughness of a region shot-peened in the trial peening step and evaluating an extent of shot peening treatment in the trial peening step based on measurement results, the evaluation step being carried out after the trial peening step but before shot-peening the surface of the water cooling hole.

With the shot peening evaluation method according to one aspect of the present invention, in the trial peening step, a shot peening process is applied to the back face of the mold in which an opening of a closed-end water cooling hole is formed, the trial peening step being carried out before shot-peening the surface of the water cooling hole in the mold. Also, the evaluation step is carried out after the trial peening step but before shot-peening the surface of the water cooling hole. In the evaluation step, at least one of the compressive residual stress and surface roughness of the region shot-peened in the trial peening step is measured and the extent of shot peening treatment in the trial peening step is evaluated based on the measurement results.

The peening conditions set in the trial peening step and evaluation made in the evaluation step can be used to set desirable peening conditions for the surface of the water cooling hole. Then, if peening conditions for the surface of the water cooling hole are established based on the peening conditions for the trial peening step and the evaluation results produced in the evaluation step and the surface of the water cooling hole in the mold is shot-peened under the established peening conditions, the surface of the water cooling hole in the mold can be shot-peened under desirable peening conditions.

In the shot peening evaluation method according to one aspect of the present invention, the trial peening step and the evaluation step may be carried out alternately a plurality of times before shot-peening the surface of the water cooling hole.

With the shot peening evaluation method according to one aspect of the present invention, since the trial peening step and the evaluation step are carried out alternately a plurality of times before shot-peening the surface of the water cooling hole, more desirable peening conditions can be found.

The shot peening evaluation method according to one aspect of the present invention further comprises: a jig fixing step of fixing a jig in which a through-hole is formed to the back face of the mold with an open end of the through-hole turned to the back face of the mold, where the through-hole is set to be equal in diameter and depth to the water cooling hole; and a trial nozzle-insertion step of inserting a shot peening nozzle into the through-hole after the jig fixing step, wherein the jig fixing step and trial nozzle-insertion step are preparatory steps before starting the trial peening step.

With the shot peening evaluation method according to one aspect of the present invention, the jig fixing step and trial nozzle-insertion step are carried out as preparatory steps before starting the trial peening step. In the jig fixing step, a jig in which a through-hole set to be equal in diameter and depth to the water cooling hole is formed is fixed to the back face of the mold with the open end of the through-hole turned to the back face of the mold. In the trial nozzle-insertion step carried out after the jig fixing step, a shot peening nozzle is inserted into the through-hole. Consequently, when the shot peening process is performed with the nozzle inserted in the water cooling hole, since practical trials can be carried out in the trial nozzle-insertion step and trial peening step and the extent of shot peening treatment in the trial peening step is evaluated in the evaluation step, excessive application of the shot peening process to the water cooling hole surface can be avoided.

In the shot peening evaluation method according to one aspect of the present invention, in the jig fixing step, pressing forces directed toward where the jig and the back face of the mold face each other may be imparted to a sealing unit placed by surrounding the open end of the through-hole in an opposing area between the jig and the back face of the mold.

With the shot peening evaluation method according to one aspect of the present invention, since in the jig fixing step, pressing forces directed toward where the jig and the back face of the mold face each other are imparted to the sealing unit placed by surrounding the open end of the through-hole in the opposing area between the jig and the back face of the mold, the sealing unit prevents air leakage from between the jig and the back face of the mold during the shot peening process in the trial peening step. That is, a process environment of the trial peening step can be configured to more closely approximate a process environment in which the surface of the closed-end water cooling hole of the mold is shot-peened, consequently making it possible to improve the accuracy of the peening conditions to be set.

A shot peening evaluation assembly structure according to one aspect of the present invention comprises: a mold with a closed-end water cooling hole formed on a back side opposite a parting-face side; and a jig in which a through-hole set to be equal in diameter and depth to the water cooling hole is formed and which is fixed to a back face of the mold with an open end of the through-hole turned to the back face of the mold.

With the shot peening evaluation assembly structure according to one aspect of the present invention, the mold has a closed-end water cooling hole formed on the back side opposite the parting-face side while a through-hole set to be equal in diameter and depth to the water cooling hole is formed in the jig. Besides, the jig is fixed to a back face of the mold with an open end of the through-hole turned to the back face of the mold.

Thus, for example, in the case of shot-peening a bottom surface of the water cooling hole with the shot peening nozzle inserted in the water cooling hole of the mold, the shot peening process can be applied as a practical trial to the back face of the mold with the nozzle inserted in the through-hole of the jig. Then, it is useful in setting desirable peening conditions for the surface of the water cooling hole to measure at least one of the compressive residual stress and surface roughness of the shot-peened region on the back face of the mold and evaluate the extent of shot peening treatment based on the measurement results.

The shot peening evaluation assembly structure according to one aspect of the present invention may further comprise a sealing unit installed in an opposing area between the jig and the back face of the mold by being placed so as to surround the open end of the through-hole and by being imparted with pressing forces directed toward where the jig and the back face of the mold face each other.

With the shot peening evaluation assembly structure according to one aspect of the present invention, since the sealing unit is placed in the opposing area between the jig and the back face of the mold so as to surround the open end of the through-hole and imparted with pressing forces directed toward where the jig and the back face of the mold face each other, when the back face of the mold is shot-peened with the shot peening nozzle inserted in the through-hole of the jig, the sealing unit prevents air leakage from between the jig and the back face of the mold. That is, the process environment in which the back face of the mold is shot-peened can be configured to more closely approximate the process environment in which the surface of the water cooling hole in the mold is shot-peened.

Advantageous Effects of Invention

As described above, the shot peening method according to one aspect of the present invention has the advantage of being able to shot-peen the surface of the water cooling hole under desirable peening conditions.

Also, the shot peening evaluation method according to one aspect of the present invention has the advantage of being useful in setting desirable peening conditions for the surface of the water cooling hole.

Also, the shot peening evaluation assembly structure according to one aspect of the present invention has the advantage of being useful in setting desirable peening conditions for the surface of the water cooling hole.

DESCRIPTION OF EMBODIMENTS

A shot peening method, shot peening evaluation method, and shot peening evaluation assembly structure according to an embodiment of the present invention will be described with reference to FIGS. 1 to 4.

(Configuration of Peening Apparatus, Mold, and the Like)

Figure 1:
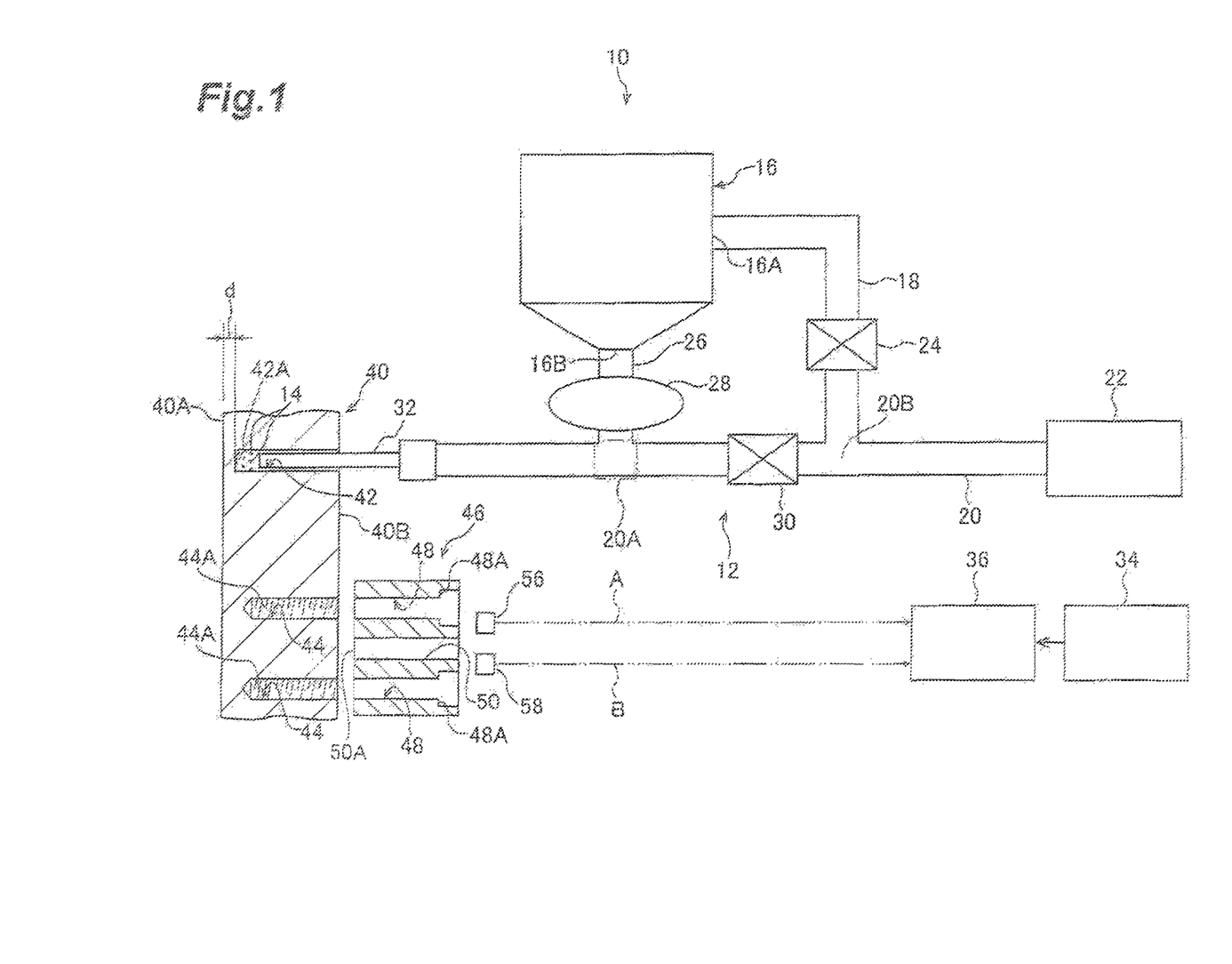
FIG. 1 is a schematic diagram showing a peening apparatus applied to a shot peening method and shot peening evaluation method according to an embodiment of the present invention.
Figure 2:
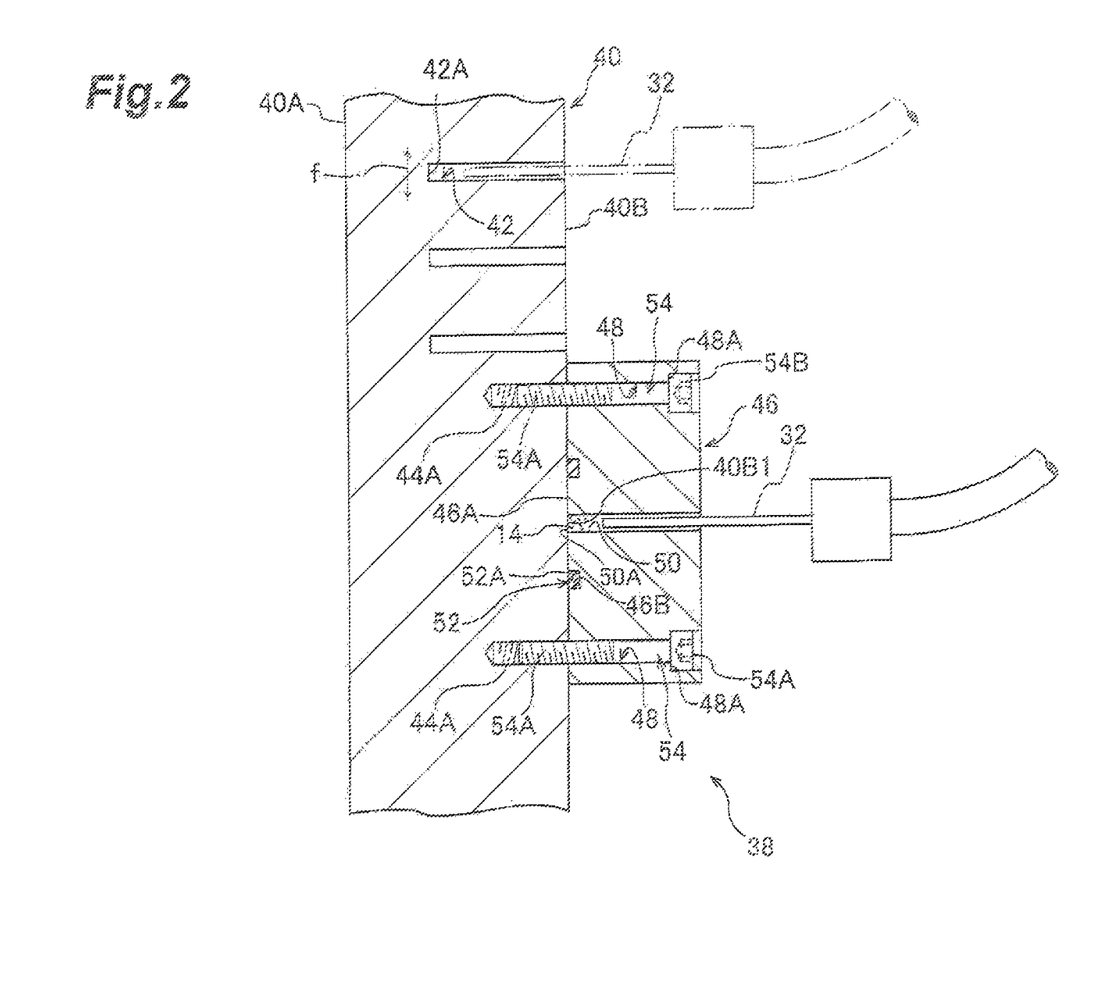
FIG. 2 is a sectional view for illustrating the shot peening method, shot peening evaluation method, and shot peening evaluation assembly structure according to the embodiment of the present invention.

FIG. 1 is a schematic diagram showing a peening apparatus 10 and the like applied to the shot peening method and shot peening evaluation method according to the present embodiment. FIG. 2 is a sectional view for illustrating the shot peening method, shot peening evaluation method, and shot peening evaluation assembly structure 38 according to the present embodiment. The peening apparatus 10 as well as a mold 40 to be peened will be described first.

As shown in FIG. 1, the peening apparatus 10 includes an ejection unit 12. The ejection unit 12 is used to eject (hurl) shot media 14 to (at) an object to be processed (the mold 40, according to the present embodiment) and equipped with a tank 16 for use to supply the shot media 14. In the present embodiment, metal balls are used as the shot media 14 (also referred to as shot or shot material), and the Vickers hardness of the metal balls are approximately equal to or higher than the object to be processed.

An air inlet port 16A is formed in upper part of the tank 16 and connected with one end of a connecting pipe 18. Another end of the connecting pipe 18 is connected to a connecting portion 20B located in a midsection of a connecting pipe 20 along a flow path while one end of the connecting pipe 20 on an upstream side (right side in FIG. 1) along the flow path is connected to a compressor 22 (compressed-air supply device) for use to supply compressed air. That is, the tank 16 is connected to the compressor 22 via the connecting pipes 18 and 20. Also, an airflow control valve 24 (electro-pneumatic proportional valve) is installed in a midsection of the connecting pipe 18 along the flow path, and when the airflow control valve 24 is opened, compressed air is supplied into the tank 16 from the compressor 22. This makes it possible to pressurize the inside of the tank 16.

Also, a shot outlet port 16B is formed in lower part of the tank 16 with a cut gate (not shown) provided therein and is connected with one end of a connecting pipe 26. Another end of the connecting pipe 26 is connected to a midsection of the connecting pipe 20 along the flow path on a downstream side of the connecting portion 20B, and a shot flow control valve 28 is installed in a midsection of the connecting pipe 26 along the flow path. For example, a Magna valve, mixing valve, or the like can be used as the shot flow control valve 28. A junction of the connecting pipe 20 with the connecting pipe 26 is configured to serve as a mixing unit 20A. On the upstream side (right side in FIG. 1) of the mixing unit 20A along the flow path, but on the downstream side (left side in FIG. 1) of the connecting portion 20B along the flow path, an airflow control valve 30 (electro-pneumatic proportional valve) is installed in the connecting pipe 20.

That is, when the cut gate and shot flow control valve 28 are opened with the inside of the tank 16 pressurized and the airflow control valve 30 is opened, the shot media 14 supplied from the tank 16 and the compressed air supplied from the compressor 22 are designed to be mixed by the mixing unit 20A and flow to the downstream side (left side in FIG. 1) of the connecting pipe 20 along the flow path.

An end of the connecting pipe 20 on the downstream side along the flow path is connected with an ejection (shot peening) nozzle 32. Consequently, the shot media 14 flowing to the mixing unit 20A is ejected from a tip of nozzle 32 by being mixed with compressed air. The nozzle 32 used has a cylindrical shape and such a diameter as to allow insertion of the nozzle 32 into a water cooling hole 42 of the mold 40.

Incidentally, the peening apparatus 10 may be configured to include a robot arm (not shown) adapted to grip the nozzle 32 and the robot arm may be configured to move the nozzle 32 forward and backward (reciprocate the nozzle 32) with respect to the water cooling hole 42.

The peening apparatus 10 is equipped with an operation unit 34. The operation unit 34 is configured to accept input of process conditions (some of peening conditions including, for example, pressure of the compressed air supplied from the compressor 22 and quantity of shot media 14 to be ejected) for the shot peening process and is configured to output a signal to a control unit 36 according to an input operation. The control unit 36 includes, for example, a storage device, processing unit, and the like and is configured to control the compressor 22, airflow control valves 24 and 30, shot flow control valve 28, the above-described cut gate (not shown), and the like based on the signal outputted from the operation unit 34. That is, the control unit 36 prestores a program configured to perform the shot peening process under peening conditions corresponding to the signal outputted from the operation unit 34.

On the other hand, an aesthetic surface 40A of the mold 40 on the parting-face side has been formed into a shape for use in molding. In contrast, plural small-diameter, closed-end water cooling holes 42 (see FIG. 2) are formed on the side of a back face 40B (face opposite the aesthetic surface 40A) of the mold 40, extending in a thickness direction of the mold 40. Although a bottom 42A of each water cooling hole 42 are illustrated as being flat in FIGS. 1 and 2, the bottom 42A of each water cooling hole 42 may be inwardly tapered or hemispherically concave.

The mold 40 according to the present embodiment is a die-casting mold made of an alloy subjected to a nitriding process (according to the present embodiment, for example, nitrocarburized SKD-61 material). Die casting is a type of metal mold casting and is a casting method which involves injecting molten metal into a mold 40 under pressure to produce large quantities of castings with high dimensional accuracy in a short time. Such molds 40 are exposed to high temperatures when molten metal is injected under pressure and are cooled during water-cooling using the water cooling holes 42. A distance d between the bottom 42A of the water cooling hole 42 and the aesthetic surface 40A is set to be short to cool the mold 40 quickly.

The nitriding process applied to the mold 40 is a heat treatment which involves heating an alloy steel containing, for example, at least one of Al, Cr, Mo, Ti, and V, in an $NH_3$ gas at low temperatures of somewhere around 500° C. to obtain an extremely hard nitrided layer on the surface thereof. The nitrided layer basically includes a diffusion layer on an alloy-steel side of base material and a compound layer on a surface side. The diffusion layer is a layer of alloy steel in which nitrogen has diffused. Also, the compound layer has nitrides, carbides, and carbonitrides, or the like, as main constituents and has the properties of being very hard and brittle. The nitrided layer may include only a diffusion layer as a sound layer from the beginning. Here, the "sound layer" according to the present embodiment means a layer thick enough to be recognized as being in normal layer conditions.

Plural closed-end bolt holes 44 are formed in locations devoid of water cooling holes 42 in the back face 40B of the mold 40, extending in a thickness direction of the mold 40. The bolt holes 44 are used to fix a jig 46 described later. A female thread 44A is formed on an inner surface of each bolt hole 44.

The jig 46 is used for evaluation of shot peening. Plural bolt insertion holes 48 for use to fix the jig 46 to the mold 40 are formed by penetrating the jig 46. Formation locations of the plural bolt insertion holes 48 are set to coincide with the bolt holes 44 at fixing locations of the jig 46 to the mold 40. Also, a countersink 48A is formed in each bolt insertion hole 48 to seat a head 54B of a bolt 54 shown in FIG. 2.

As shown in FIG. 2, the bolts 54 clamp the jig 46 between the heads 54B and mold 40 as male threads 54A penetrating the bolt insertion holes 48 in the jig 46 are screwed into the female threads 44A in the mold 40. That is, the jig 46 is fastened to the mold 40 with the bolts.

A through-hole 50 is formed in the jig 46. Penetration direction of the through-hole 50 is set to be parallel to penetration direction of the bolt insertion holes 48. The through-hole 50 in the jig 46 is set to be dimensionally equal in diameter to the water cooling holes 42 in the mold 40. Also, the through-hole 50 in the jig 46 is set to be dimensionally equal in depth (length in the left-to-right direction in FIG. 2) to the water cooling holes 42 in the mold 40.

The jig 46 is fixed to the back face 40B of the mold 40 with an open end 50A of the through-hole 50 turned to the back face 40B. The mold 40, jig 46, and bolts 54 make up the shot peening evaluation assembly structure 38.

A mounting groove 46B used to mount an annular sealing member 52A is formed on a seating face 46A of the jig 46, the seating face 46A acting as an opposing area between the jig 46 and the back face 40B of the mold 40. When viewed in a direction perpendicular to the seating face 46A, the mounting groove 46B is formed into an annular shape, surrounding the open end 50A of the through-hole 50. The sealing member 52A mounted by being fitted in the mounting groove 46B makes up a sealing unit 52. The sealing unit 52 is placed so as to surround the open end 50A of the through-hole 50, and is imparted with pressing forces directed toward where the jig 46 and the back face 40B of the mold 40 face each other, when the bolts 54 are tightened. From the viewpoint of easy handling, desirably the sealing member 52A making up the sealing unit 52 is mounted in such a way as to be kept by its own tension from falling off even if an open side of the mounting groove 46B is turned downward.

Thus, the through-hole 50 in the jig 46 and a trial-machined area 40B1 facing the open end 50A of the through-hole 50 on the back face 40B of the mold 40 are integrated into a structural portion which patterns after the water cooling holes 42 of the mold 40.

Also, as shown in FIG. 1, the peening apparatus 10 is equipped with a residual stress measuring device 56 (e.g., an x-ray diffraction residual stress measuring device) intended to measure compressive residual stress at a predetermined region of the mold 40. Also, the peening apparatus 10 is equipped with a surface roughness measuring device 58 intended to measure surface roughness at a predetermined region of the mold 40.

Incidentally, although in the present embodiment, the residual stress measuring device 56 and surface roughness measuring device 58 are installed as part of the peening apparatus 10, the residual stress measuring device 56 and surface roughness measuring device 58 may be installed independently of the peening apparatus 10. Also, an equipment configuration may be adopted in which the residual stress measuring device 56 and surface roughness measuring device 58 are each connected to the control unit 36 (see chain double-dashed lines A and B in FIG. 1) to output measurement results produced by the residual stress measuring device 56 and measurement results produced by the surface roughness measuring device 58 to the control unit 36.

(shot Peening method and shot peening evaluation method)

Figure 3:
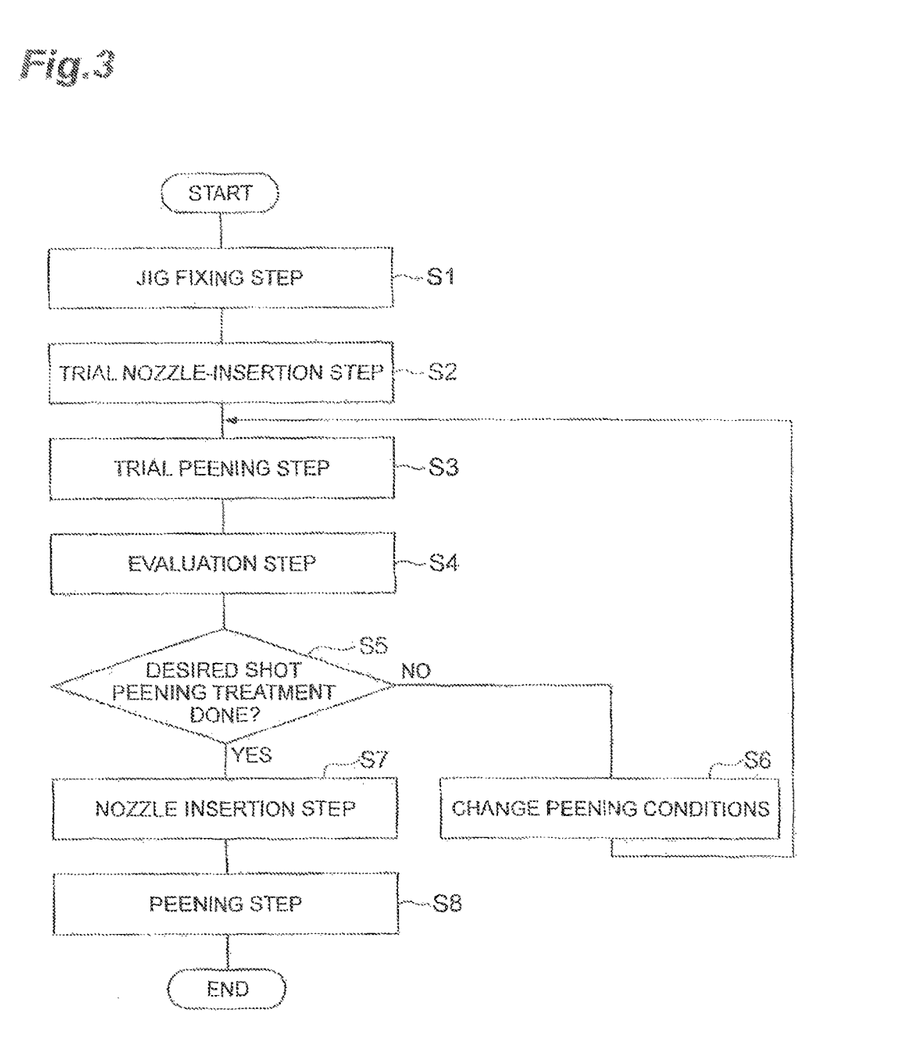
FIG. 3 is a flowchart showing the shot peening method and shot peening evaluation method according to the embodiment of the present invention.

Next, a shot peening method and shot peening evaluation method as well as operation and effects thereof will be described with reference to FIG. 3. FIG. 3 is a flowchart showing the shot peening method and shot peening evaluation method.

In the shot peening method and shot peening evaluation method, a jig fixing step is carried out first (step S1). In the jig fixing step, the jig 46 in which the through-hole 50 shown in FIG. 2 is formed is fastened to the back face 40B of the mold 40 using bolts, with the open end 50A of the through-hole 50 turned to the back face 40B of the mold 40. Also, in the jig fixing step, pressing forces directed toward where the jig 46 and the back face 40B of the mold 40 face each other are imparted to the sealing unit 52 placed by surrounding the open end 50A of the through-hole 50 in the opposing area between the jig 46 and the back face 40B of the mold 40. Next, a trial nozzle-insertion step is carried out (step S2). In the trial nozzle-insertion step, the shot peening nozzle 32 is inserted into the through-hole 50 in the jig 46. The jig fixing step and trial nozzle-insertion step are carried out as preparatory steps before starting a trial peening step described next.

Next, the trial peening step is carried out (step S3). In the trial peening step, a shot peening process is applied to the back face 40B of the mold 40 in which the openings of the closed-end water cooling holes 42 are formed. During the shot peening process in the trial peening step, the sealing unit 52 prevents air leakage from between the jig 46 and the back face 40B of the mold 40. Consequently, a process environment of the trial peening step can very closely approximate a process environment in which the surfaces of the closed-end water cooling holes 42 in the mold 40 are shot-peened (peening step described later).

After the trial peening step, the jig 46 is removed from the back face 40B of the mold 40, and an evaluation step is carried out subsequently (step S4). In the evaluation step, the compressive residual stress and surface roughness of the region shot-peened in the trial peening step are measured (condition of the processed region is checked, in a wider sense) and the extent of shot peening treatment in the trial peening step is evaluated based on the measurement results. The evaluation of the trial peening step may be made, for example, by a program prestored by the control unit 36 (see FIG. 1). The peening conditions in the trial peening step and the evaluation in the evaluation step are used to set desirable peening conditions for the surfaces (inner surfaces) of the water cooling holes 42. According to the present embodiment, the peening conditions include conditions for the type of shot media 14, pressure of the compressed air supplied from the compressor 22 (see FIG. 1), and quantity of shot media 14 to be ejected.

Incidentally, although in the evaluation step according to the present embodiment, the compressive residual stress and surface roughness of the region shot-peened in the trial peening step are measured and the extent of shot peening treatment in the trial peening step is evaluated based on the measurement results, as a variation of the present embodiment, one of the compressive residual stress and surface roughness of the region shot-peened in the trial peening step may be measured in the evaluation step and the extent of shot peening treatment in the trial peening step may be evaluated based on the measurement results. That is, it is sufficient if at least one of the compressive residual stress and surface roughness of the region shot-peened in the trial peening step is used as a parameter to be evaluated in the evaluation step.

Also, as described above, since the sealing unit 52 is installed on the jig 46, the trial peening step can be carried out in an environment which very closely approximates that of the peening step, improving the accuracy of the peening conditions to be set.

The jig fixing step, trial nozzle-insertion step, trial peening step, and evaluation step described above are some of the steps of the shot peening method and all of the steps of the shot peening evaluation method.

Next, according to the present embodiment, it is determined whether or not desired compressive residual stress or surface roughness (desired shot peening treatment) has been given to the trial-machined area 40B1 (step S5). If it is determined that the desired shot peening treatment has not been done in step S5, the peening conditions are changed (step S6), and the trial peening step and the evaluation step may be repeated until the desired shot peening treatment is done. The peening conditions obtained by repeating steps S3 to S6 are desirable peening conditions set based on evaluation results produced in the evaluation step. In so doing, either a same region or different regions on the back face 40B of the mold 40 may be shot-peened in the trial peening step. If different regions on the back face 40B of the mold 40 are shot-peened in multiple repetitions of the trial peening step, this means that the back face 40B of the mold 40 is shot-peened under peening conditions differing among the multiple repetitions of the trial peening step.

If it is determined that the desired shot peening treatment has been done in step S5, the nozzle insertion step is carried out (step S7). In the nozzle insertion step, the shot peening nozzle 32 is inserted into each water cooling hole 42 (see the chain double-dashed lines). Consequently, even if the water cooling hole 42 is small in diameter and deep, the high-velocity shot media can be caused to hit the bottom of the water cooling hole 42. According to the present embodiment, an insertion length of the nozzle 32 into each water cooling hole 42 in the nozzle insertion step is equal to that of the nozzle 32 into the through-hole 50 in the trial nozzle-insertion step. The nozzle-insertion step is carried out as a preparatory step before starting a peening step described next.

Next, the peening step is carried out (step S8). In the peening step, the surface (inner surface) of the water cooling hole 42 in the mold 40 is shot-peened under the peening conditions set based on the peening conditions for the trial peening step and the evaluation results produced in the evaluation step. This makes it possible to shot-peen the surface of the water cooling hole 42 under desirable peening conditions.

In other words, a practical trial of the nozzle insertion step is carried out in the trial nozzle-insertion step, a practical trial of the peening step is carried out in the trial peening step, and the extent of shot peening treatment in the trial peening step is evaluated in the evaluation step, making it possible, for example, to avoid excessive application of the shot peening process.

Also, according to the present embodiment, since the peening conditions for the peening step are set based on the peening conditions for the trial peening step repeated multiple times and the evaluation results produced in the evaluation step repeated multiple times, the surfaces of the water cooling holes 42 can be shot-peened under more desirable (close to ideal) peening conditions. Incidentally, if the same region on the back face 40B of the mold 40 is shot-peened in the trial peening step repeated multiple times, the peening conditions for the trial peening step used as decision-making information in setting the peening conditions for the peening step are cumulative peening conditions for the trial peening step.

As described above, the shot peening method according to the present embodiment makes it possible to shot-peen the surfaces of the water cooling holes 42 under desirable peening conditions. Also, the shot peening evaluation method and shot peening evaluation assembly structure 38 according to the present embodiment can be used to set desirable peening conditions for the surfaces of the water cooling holes 42.

If compressive residual stress can be imparted effectively to the surfaces of the water cooling holes 42 by shot-peening the surfaces of the water cooling holes 42 under desirable peening conditions, stress corrosion cracking (SCC) around the water cooling holes 42 of the mold 40 can consequently be prevented or effectively reduced.

Now, a supplementary explanation of stress corrosion cracking will be provided. The aesthetic surface 40A of the mold 40 is exposed to high temperatures when molten metal is injected under pressure, and subsequently the mold 40 is cooled during water-cooling done by causing cooling water to flow into the water cooling holes 42. As this cycle is repeated successively, heat checks or heat cracks could possibly occur, which could cause mold breakage. When the distance between the water cooling holes 42 and aesthetic surface 40A is short, there is a steep thermal gradient, increasing thermal stress (tensile stress f) received by the surfaces of the water cooling holes 42 and thereby increasing the possibility of stress corrosion cracking.

There are generally three contributing factors to stress corrosion cracking, namely, a material factor, an environmental factor, and tensile stress f; and stress corrosion cracking occurs when the three factors overlap. However, the present embodiment imparts compressive residual stress by performing the shot peening process under desirable peening conditions, thereby curbs the influence of the tensile stress f which is one of the contributing factors to stress corrosion cracking, and eventually curbs generation of stress corrosion cracking.

When small-diameter, deep, blind, water cooling holes 42 (closed-end, narrow, deep holes) are shot-peened, the compressed air injected into the water cooling holes 42 from the nozzle 32 does not escape easily. In such a case, velocity of the shot media 14 mixed with the compressed air does not increase so easily as when a shot peening process is performed in open space. If the velocity of the shot media 14 mixed with the compressed air falls short of a required velocity as a result, it is conceivable that the shot peening process may not produce a sufficient effect at the bottom 42A (terminal portion) of the water cooling hole 42. However, with the present embodiment, since the surface of each water cooling hole 42 is shot-peened by ejection of the shot media 14 together with the compressed air from the nozzle 32 inserted in the water cooling hole 42, even if the blind, water cooling holes 42 are small in diameter and deep, the high-velocity shot media 14 can be caused to hit the bottom 42A of the water cooling hole 42. Thus, compressive residual stress can be imparted effectively to the bottom 42A of the water cooling hole 42.

On the other hand, depending on the presence or absence of a nitrided layer on the surfaces of the water cooling hole 42, it is conceivable that compressive residual stress cannot be imparted effectively, and thus it is important to perform the shot peening process under desirable peening conditions. To clarify this point, hot-work tool steel SKD-61 is often used as a material for the die-casting mold 40 and a nitriding process is often applied to the mold 40 as a heat treatment. Besides, one of the points to note in shot-peening the mold 40 subjected to the nitriding process is removal (stock removal) of nitrided layers (a compound layer and diffusion layer). When the shot peening process is performed under a strong peening condition, the nitrided layer is scraped as well, but the nitrided layer and a directly underlying layer (base material or substrate) have different mechanical properties and differ greatly in the residual stress imparted as a result of the shot peening process.

Figure 4:
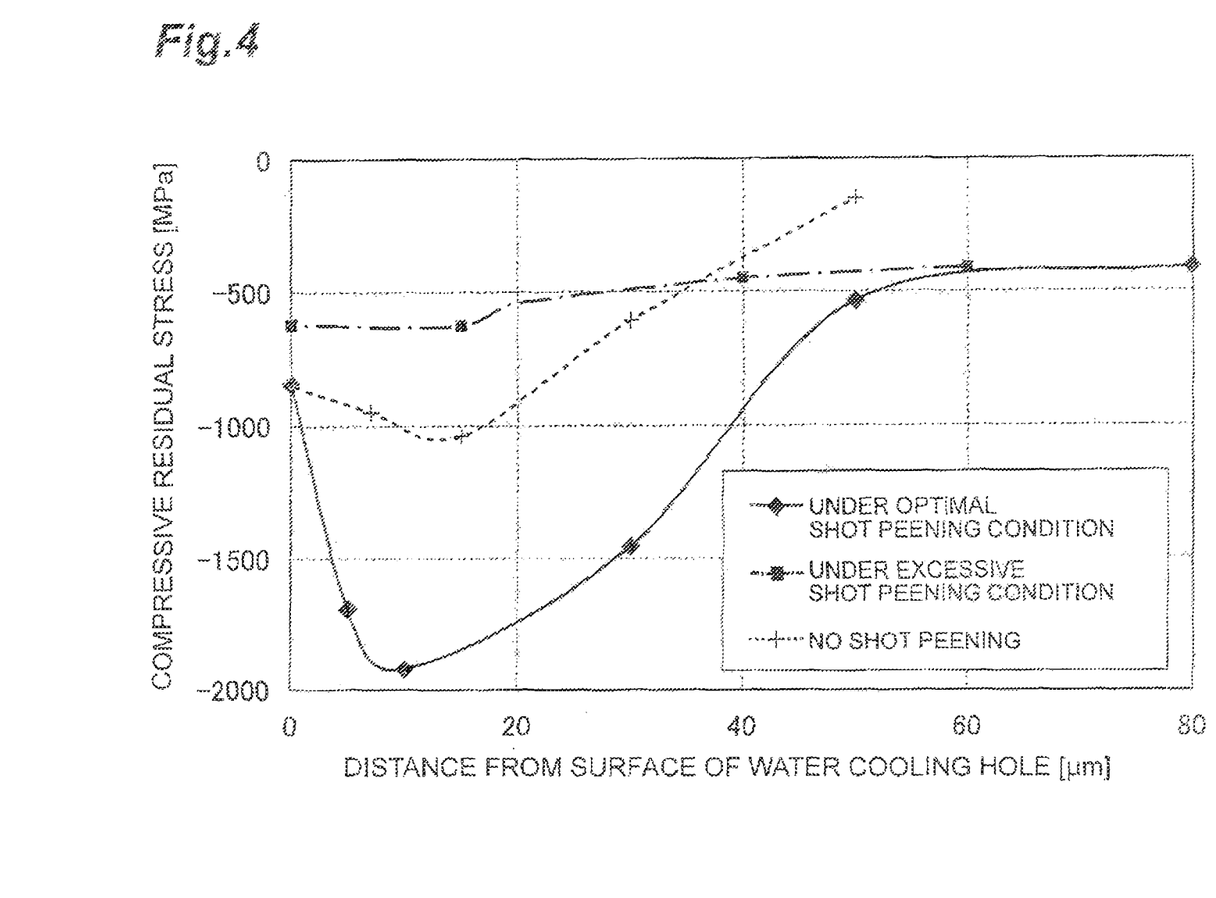
FIG. 4 is a graph showing distributions of compressive residual stress under conditions in which a shot peening process is applied optimally, applied excessively, and not applied, respectively.

FIG. 4 shows results of measuring distributions of compressive residual stress under conditions in which a shot peening process is applied optimally, applied excessively, and not applied, respectively. The abscissa represents the distance from the surface of the water cooling hole 42 (depth from the surface in a direction perpendicular to the base material of the mold 40). As can be seen from FIG. 4, if a region has a nitrided layer before the shot peening process and the nitrided layer is removed from the region due to excessive application of the shot peening process, compressive residual stress cannot be imparted effectively to the target region. Under a condition in which it is assumed that the shot peening process is applied to the base material due to scraping of the nitrided layer during shot peening, the residual stress which can be imparted is less than the residual stress imparted during nitriding. That is, the state of compressive residual stress on the surface of the water cooling hole 42 is consequently worse than that before the application of the shot peening process.

On this point, in the present embodiment, since the surfaces of the water cooling holes 42 in the mold 40 shown in FIG. 2 are shot-peened under the peening conditions set based on the peening conditions for the trial peening step and the evaluation results produced in the evaluation step, compressive residual stress is imparted effectively to the surfaces of the water cooling holes 42.

To give a supplementary explanation from another point of view, generally conditions of a heat treatment (nitriding process) applied to workparts (molds, according to the present embodiment) vary from workpart to workpart, and so does the extent of nitriding applied to the workparts. This makes it necessary to set peening conditions (shot peening conditions) for each mold 40 to be processed, within the bounds of not removing the nitrided layer. Basically, an extended duration of the shot peening process could result in removal of the nitrided layer, and thus the processing time needs to be set properly. Also, effects of shot peening is affected by differences in the material and heat treatment (nitriding process) or the like of the workpart (mold, according to the present embodiment). Therefore, it is important to set desirable peening conditions for each mold 40 to be processed.

However, according to the present embodiment, since the trial peening step and evaluation step are carried out for each mold 40 to be processed and the extent of shot peening treatment is evaluated before the peening step is carried out, the surfaces of the water cooling holes 42 can be shot-peened (treated) under more reliable peening conditions.

(Supplementary explanation of embodiment)

With the shot peening method and shot peening evaluation method according to the above embodiment, the trial peening step and evaluation step are carried out alternately a plurality of times before the peening step and this is desirable, but the shot peening method and shot peening evaluation method may be configured to carry out each of the trial peening step and evaluation step once.

Also, although the jig fixing step and trial nozzle-insertion step are carried out in the shot peening method and shot peening evaluation method according to the above embodiment, when, for example, the surfaces of large-diameter, shallow water cooling holes are shot-peened and the peening step is carried out without inserting the nozzle into the water cooling holes, the jig fixing step and trial nozzle-insertion step may be omitted.

Also, in the jig fixing step according to the above embodiment, pressing forces directed toward where the jig 46 and the back face 40B of the mold 40 face each other are imparted to the sealing unit 52 placed by surrounding the open end 50A of the through-hole 50 in the opposing area between the jig 46 and the back face 40B of the mold 40, and this configuration is desirable, but if sealing between the jig 46 and the back face 40B of the mold 40 is ensured even if such a sealing unit 52 is not provided, a configuration without a sealing unit may be adopted.

Also, although in the above embodiment, the jig 46 is fastened to the mold 40 with bolts, the jig may be fixed to the mold using another fixing structure: for example, the jig and mold may be clamped in a vice or the like.

Furthermore, the concept of "being equal in diameter and depth" described in the appended claims includes not only cases of being equal in diameter and depth in the strict sense as with the above embodiment, but also cases of being recognized as being substantially equal in diameter and depth, if not being equal in diameter and depth in the strict sense, and of providing substantially the same operation and effects as being equal in diameter and depth in the strict sense. For example, when the bottom of the water cooling hole is inwardly tapered or hemispherically concave, if the depth of the through-hole of the jig is equal to the depth of the water cooling hole excluding the inwardly tapered or concave portion, the water cooling hole and through-hole may sometimes be recognized as being substantially equal in depth.

Note that the embodiment and plural variation described above may be implemented in combination as appropriate.

REFERENCE SIGNS LIST

10: peening apparatus; 12: ejection unit; 14: shot media; 16: tank; 18: connecting pipe; 20: connecting pipe; 20A: mixing unit; 20B: connecting portion; 22: compressor; 24: airflow control valve; 26: connecting pipe; 28: shot flow control valve; 30: airflow control valve; 32: nozzle; 34: operation unit; 36: control unit; 38: shot peening evaluation assembly structure; 40: mold; 40A: aesthetic surface (parting face); 40B: back face (back face of the mold); 40B1: trial-machined area; 42: water cooling hole; 42A: bottom; 44: bolt hole; 46: jig; 48: bolt insertion hole; 50: through-hole; 50A: open end; 52: sealing unit; 54: bolt; 56: residual stress measuring device; 58: surface roughness measuring device.

The invention claimed is:

1. A shot peening evaluation assembly structure comprising:
    a mold with a closed-end water cooling hole formed on a back side of the mold opposite a parting-face side; and
    a jig in which a through-hole set to be equal in diameter and depth to the water cooling hole is formed and which is fixed to a back face of the back side of the mold with an open end of the through-hole turned to the back face of the mold;
    wherein, the through-hole of the jig and the back face of the mold are configured to approximate a shot peening process environment for the water cooling hole such that trial peening is performed using the jig to evaluate desirable peening conditions for the water cooling hole.

2. The shot peening evaluation assembly structure according to claim 1, further comprising a sealing unit installed in an opposing area between the jig and the back face of the mold by being placed so as to surround the open end of the through-hole and by being imparted with pressing forces directed toward where the jig and the back face of the mold face each other.

* * * * *